(12) United States Patent
Baileykobayashi et al.

(10) Patent No.: US 12,392,770 B2
(45) Date of Patent: Aug. 19, 2025

(54) FOREIGN SUBSTANCE INTRODUCTION CONSTRUCT AND USE THEREOF

(71) Applicant: TOAGOSEI CO., LTD., Tokyo (JP)

(72) Inventors: Nahoko Baileykobayashi, Tsukuba (JP); Tetsuhiko Yoshida, Tsukuba (JP)

(73) Assignee: TOAGOSEI CO., LTD., Tokyo (JP)

( * ) Notice: Subject to any disclaimer, the term of this patent is extended or adjusted under 35 U.S.C. 154(b) by 391 days.

(21) Appl. No.: 18/177,931

(22) Filed: Mar. 3, 2023

(65) Prior Publication Data
US 2023/0280333 A1 Sep. 7, 2023

(30) Foreign Application Priority Data

Mar. 8, 2022 (JP) ................................ 2022-035236

(51) Int. Cl.
*G01N 33/50* (2006.01)
*C07K 7/08* (2006.01)

(52) U.S. Cl.
CPC ........... *G01N 33/5008* (2013.01); *C07K 7/08* (2013.01)

(58) Field of Classification Search
None
See application file for complete search history.

(56) References Cited

U.S. PATENT DOCUMENTS 11,927,589 B2 * 3/2024 Baileykobayashi et al. ................. C12N 9/12
2012/0122210 A1 5/2012 Yoshida et al.

FOREIGN PATENT DOCUMENTS

WO 2011013700 A1 2/2011

OTHER PUBLICATIONS

Bioinformatic characterisation of the effector repertoire of the strawberry pathogen *Phytophthora cactorum*, PLoS ONE 13(10): e0202305. https://doi.org/10.1371/journal. (Year: 2018).*
Goyal P, Pandey D, Siess W. Phosphorylation-dependent regulation of unique nuclear and nucleolar localization signals of LIM kinase 2 in endothelial cells. J Biol Chem. Sep. 1, 2006;281(35):25223-30. doi: 10.1074/jbc.M603399200. Epub Jul. 4, 2006. PMID: 16820362.
López-Vidal EM, Schissel CK, Mohapatra S, Bellovoda K, Wu CL, Wood JA, Malmberg AB, Loas A, Gómez-Bombarelli R, Pentelute BL. Deep Learning Enables Discovery of a Short Nuclear Targeting Peptide for Efficient Delivery of Antisense Oligomers. JACS Au. Oct. 6, 2021;1(11):2009-2020. doi: 10.1021/jacsau.1c00327. PMID: 34841414; PMCID: PMC8611673.

* cited by examiner

*Primary Examiner* — Robert A Wax
(74) *Attorney, Agent, or Firm* — Young Basile Hanlon & MacFarlane, P.C.

(57) ABSTRACT

The herein disclosed method for introducing a foreign substance of interest from outside a eukaryotic cell into at least a cytoplasm of the cell, comprises: (1) a step of preparing a foreign substance introduction construct that has a carrier peptide fragment comprising either of the amino acid sequences: KKRTLRKSNRKKRWPC(SEQ ID NO: 1) and KKRTLRKKKRKKRWPC(SEQ ID NO: 2), and that has the foreign substance of interest bonded to an N-terminal side and/or C-terminal side of the carrier peptide fragment; (2) a step of supplying the foreign substance introduction construct into a sample that contains a target eukaryotic cell; and (3) a step of incubating the sample into which the foreign substance introduction construct has been supplied, to thereby introduce the construct into the eukaryotic cell in the sample.

9 Claims, 1 Drawing Sheet
Specification includes a Sequence Listing.

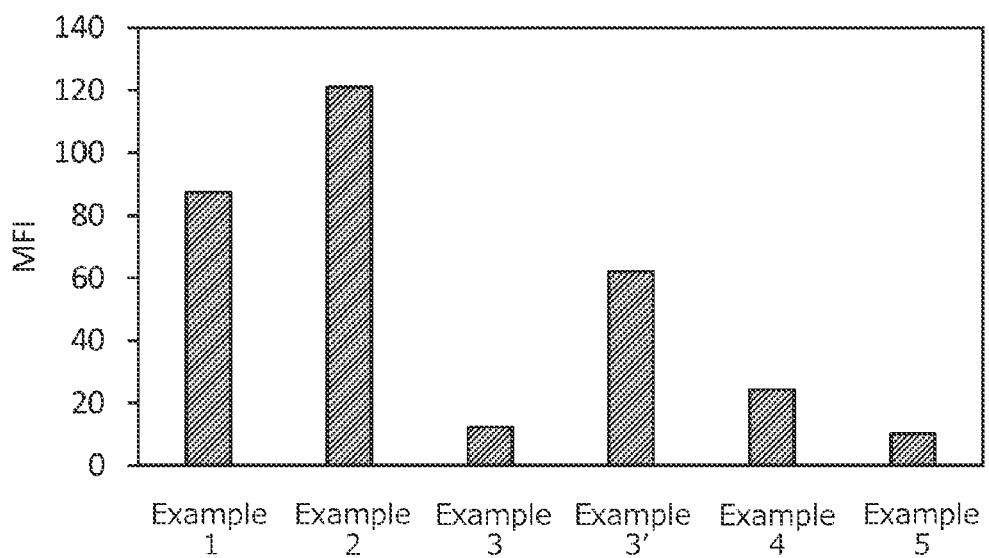

SEQUENCE LISTING

```
Sequence total quantity: 9
SEQ ID NO: 1              moltype = AA  length = 16
FEATURE                   Location/Qualifiers
source                    1..16
                          mol_type = protein
                          organism = synthetic construct
SEQUENCE: 1
KKRTLRKSNR KKRWPC                                                    16

SEQ ID NO: 2              moltype = AA  length = 16
FEATURE                   Location/Qualifiers
source                    1..16
                          mol_type = protein
                          organism = synthetic construct
SEQUENCE: 2
KKRTLRKKKR KKRWPC                                                    16

SEQ ID NO: 3              moltype = AA  length = 13
FEATURE                   Location/Qualifiers
source                    1..13
                          mol_type = protein
                          organism = synthetic construct
SEQUENCE: 3
KKRTLRKNDR KKR                                                       13

SEQ ID NO: 4              moltype = AA  length = 13
FEATURE                   Location/Qualifiers
source                    1..13
                          mol_type = protein
                          organism = synthetic construct
SEQUENCE: 4
KKRTLRKSNR KKR                                                       13

SEQ ID NO: 5              moltype = AA  length = 13
FEATURE                   Location/Qualifiers
source                    1..13
                          mol_type = protein
                          organism = synthetic construct
SEQUENCE: 5
KKRTLRKKKR KKR                                                       13
```

```
SEQ ID NO: 6              moltype = AA  length = 16
FEATURE                   Location/Qualifiers
source                    1..16
                          mol_type = protein
                          organism = synthetic construct
SEQUENCE: 6
KKRTLRKNDR KKRWPC                                                              16

SEQ ID NO: 7              moltype = AA  length = 16
FEATURE                   Location/Qualifiers
source                    1..16
                          mol_type = protein
                          organism = synthetic construct
SEQUENCE: 7
KKRTLRKKRR KKRWPC                                                              16

SEQ ID NO: 8              moltype = AA  length = 16
FEATURE                   Location/Qualifiers
source                    1..16
                          mol_type = protein
                          organism = synthetic construct
SEQUENCE: 8
KKRTLRKRKR KKRWPC                                                              16

SEQ ID NO: 9              moltype = AA  length = 16
FEATURE                   Location/Qualifiers
source                    1..16
                          mol_type = protein
                          organism = synthetic construct
SEQUENCE: 9
KKRTLRKRRR KKRWPC                                                              16
```

FOREIGN SUBSTANCE INTRODUCTION CONSTRUCT AND USE THEREOF

CROSS-REFERENCE TO RELATED APPLICATIONS

This application claims priority to Japanese Patent Application No. 2022-035236, filed Mar. 8, 2022, the entire disclosure of which is hereby incorporated by reference.

REFERENCE TO SEQUENCE LISTING SUBMITTED VIA EFS-WEB

This application includes an electronically submitted sequence listing in XML format. The XML file contains a sequence listing entitled "TG22-015US.XML" which was created on Feb. 27, 2023 and is 9 kilobytes in size. The sequence listing contained in this XML file is part of the specification and is hereby incorporated by reference herein in its entirety.

TECHNICAL FIELD

The present art relates to a method for introducing (transferring) a foreign substance from outside a eukaryotic cell into an interior of the cell, and further relates to a foreign substance introduction construct used in this method.

BACKGROUND

Foreign substances and particularly bioactive substances, e.g., polypeptides, have been introduced into the cells (eukaryotic cells) of, e.g., humans and other mammals, in order to change a characteristic of the cells (as well as tissues and organs composed of the cells) or enhance or improve a function of the cells.

For example, WO 2011/013700 discloses a foreign substance introduction construct that contains a foreign substance of interest and the amino acid sequence (carrier peptide fragment) described in SEQ ID NO: 3, which is known as the nucleolar localization signal (also abbreviated as "NoLS" in the following) described in Journal of Biological Chemistry, volume 281, number 35 (2006), pp. 25223-25230. This construct can traverse a cell membrane of eukaryotic cells at high efficiencies and can thus introduce the foreign substance of interest from outside a eukaryotic cell into a cytoplasm of the cell at high efficiencies.

In An Open Access Journal of the American Chemical Society Au, volume 1, number 11 (2021), pp. 2009-2020, technology is disclosed that uses deep learning technology to predict a cell membrane-penetrating peptide comprising a low-arginine-content short amino acid sequence (approximately not more than 20 residues) having a reduced toxicity.

SUMMARY

In recent years, there has been increasing interest, from, inter alia, a therapeutic perspective, in peptides that exhibit cell membrane permeability, and there is desire for developing art for introducing foreign substances into target cells at higher efficiencies.

The present art was therefore created in order to respond to this demand, and the present disclosure takes as an object the introduction of a method of efficiently introducing a foreign substance of interest from outside a eukaryotic cell into at least a cytoplasm of the cell. An additional object of the present disclosure is to provide a foreign substance introduction construct that can efficiently bring about the introduction of a foreign substance of interest from outside a eukaryotic cell into at least the cytoplasm of the cell.

In order to introduce the foreign substance introduction construct disclosed in WO 2011/013700 from outside a eukaryotic cell into the cell cytoplasm at even higher efficiencies, the present inventors discovered that a high cell membrane permeability is exhibited by variants (for example, SEQ ID NOs: 4 and 5) in which the asparagine at position 8 and the aspartic acid at position 9 of the amino acid sequence given by SEQ ID NO: 3, in each case counting from the N-terminal side, are replaced by another amino acid. Moreover, as a result of carrying out intensive investigations in order to improve the cell membrane permeability of these variants, the present inventors discovered that the cell membrane permeability is further improved by the addition, to the C-terminal side of these variants, of tryptophan-proline-cysteine (W-P-C), which does not contain the arginine and lysine that have generally been suggested as contributing to cell membrane permeability.

The herein disclosed method is a method for introducing a foreign substance of interest from outside a eukaryotic cell into at least the cytoplasm of the cell, the method comprising: (1) a step of preparing a foreign substance introduction construct that has a carrier peptide fragment comprising either of the following amino acid sequences:

KKRTLRKSNRKKRWPC (SEQ ID NO: 1)

KKRTLRKKKRKKRWPC (SEQ ID NO: 2)

and the foreign substance of interest bonded to an N-terminal side and/or C-terminal side of the carrier peptide fragment; (2) a step of supplying the foreign substance introduction construct into a sample that contains a target eukaryotic cell; and (3) a step of incubating the sample into which the foreign substance introduction construct has been supplied, to thereby introduce the construct into the eukaryotic cell in the sample.

Here, "foreign substance" encompasses inorganic compounds and organic compounds that can be bonded, either directly or indirectly through a suitable linker, to the N-terminal side or C-terminal side of the carrier peptide fragment, and that have a molecular size and chemical characteristics that support introduction or transfer into the interior of a eukaryotic cell.

In accordance with the method having the indicated constitution, a foreign substance of interest can be efficiently introduced from outside a eukaryotic cell (outer side of the cell membrane) across the cell membrane into the cytoplasm (preferably also across a nuclear membrane into the nucleus) because the carrier peptide fragment possessed by the foreign substance introduction construct has a high cell membrane permeability.

In an aspect of the herein disclosed method, the foreign substance is any organic compound selected from the group consisting of polypeptides, nucleic acids, dyes, and drugs.

Here, "polypeptide" denotes a polymer having a structure in which a plurality of amino acids are bonded by a peptide bond. The polypeptide is not limited by the number of peptide bonds (i.e., the number of amino acid residues). Thus, polypeptides encompass compounds generally known as peptides, which have approximately from 10 to fewer than 300 amino acid residues, and compounds generally known as proteins (typically macromolecular compounds composed of at least 300 amino acid residues). Polypeptides are not rigorously distinguished from proteins in this field. In the present Specification, polypeptide is used to comprehensively refer to polymers composed of a plurality of amino acid residues (including oligomers).

In addition, "nucleic acid" refers to nucleotide polymers and encompasses DNA and RNA. This "nucleic acid" is not limited with respect to the number of bases.

In another aspect of the herein disclosed method, the foreign substance is located on the C-terminal side of the carrier peptide fragment.

This constitution enables the efficient introduction of the foreign substance of interest from outside a eukaryotic cell into at least the cytoplasm of the cell.

In another aspect of the herein disclosed method, the α-amino group of the lysine residing at the N-terminal side of the carrier peptide fragment is acetylated. This constitution can improve the intracellular stability of the construct.

In another aspect of the herein disclosed method, the target eukaryotic cell for introduction of the foreign substance introduction construct is a human cell or a cell from a nonhuman mammal.

This herein disclosed method makes it possible to efficiently introduce a foreign substance into the cytoplasm of a human cell or the cytoplasm of the cell of a nonhuman mammal.

In order to realize the aforementioned objects, the present disclosure also provides an artificially fabricated foreign substance introduction construct for the purpose of introducing (transferring) a foreign substance of interest from the outside (i.e., on the outer side of the cell membrane) of a eukaryotic cell (in particular, various animal cells lacking a cell wall, as represented by human cells and nonhuman mammalian cells) into at least the cytoplasm of the cell (preferably also into the nucleus).

That is, the herein disclosed foreign substance introduction construct has a carrier peptide fragment comprising either of the following amino acid sequences:

KKRTLRKSNRKKRWPC (SEQ ID NO: 1)

KKRTLRKKKRKKRWPC (SEQ ID NO: 2)

and the foreign substance of interest bonded to the N-terminal side and/or the C-terminal side of the carrier peptide fragment.

Due to its high cell membrane permeability, this construct can efficiently introduce a foreign substance of interest into a target eukaryotic cell.

In an aspect of the herein disclosed foreign substance introduction construct, the foreign substance is any organic compound selected from the group consisting of polypeptides, nucleic acids, dyes, and drugs.

In another aspect of the herein disclosed foreign substance introduction construct, the foreign substance is located at the C-terminal side of the carrier peptide fragment. In a preferred aspect of the herein disclosed foreign substance introduction construct, the α-amino group of the lysine residing at the N-terminal side of the carrier peptide fragment is acetylated.

BRIEF DESCRIPTION OF THE DRAWING

FIG. 1 is a graph that shows the values of the MFI obtained by flow cytometric analysis of the cells after culturing after the addition of a construct (addition) as shown in Examples 1 to 5 to a HeLa cell culture.

DETAILED DESCRIPTION

Preferred embodiments of the present art are described in the following. Matters required for the implementation of the present art, but which are not particularly described in the present Specification (for example, general matters related to methods for the chemical synthesis of peptides, cell culture techniques, and the preparation of compositions that contain peptides and/or nucleic acids as components), can be understood as design matters for the individual skilled in the art based on the conventional art in fields such as cell engineering, physiology, medicine, pharmaceutical science, organic chemistry, biochemistry, genetic engineering, protein engineering, molecular biology, genetics, and so forth.

The present art can be implemented based on the contents disclosed in the present Specification and the common general technical knowledge in the pertinent fields. In the description that follows, amino acids are represented, depending on the circumstances, by the single letter codes (except that three letter codes are used in the sequence listings) stipulated by the nomenclature for amino acids given in the IUPAC-IUB guidelines. Unless specifically indicated otherwise, in the present Specification "amino acid residue" is a term that encompasses the N-terminal amino acid and the C-terminal amino acid of a peptide chain.

In the present Specification, "synthetic peptide" refers to a peptide fragment for which the peptide chain thereof does not exist by itself in an independent and stable manner in nature, but rather is produced by artificial chemical synthesis or biosynthesis (i.e., production based on genetic engineering) and can exist in a stable manner in a prescribed composition. Herein, "peptide" is a term that indicates an amino acid polymer having a plurality of peptide bonds, and there is no limitation with regard to the number of amino acid residues.

For the amino acid sequences described in the present Specification, the left side is always the N-terminal side and the right side always indicates the C-terminal side.

The herein disclosed foreign substance introduction construct has a carrier peptide fragment comprising either of the following amino acid sequences:

KKRTLRKSNRKKRWPC (SEQ ID NO: 1)

KKRTLRKKKRKKRWPC (SEQ ID NO: 2)

and has a foreign substance of interest bonded to the N-terminal side and/or the C-terminal side of the carrier peptide fragment.

This carrier peptide fragment is a peptide prescribed (identified) by the amino acid sequence given by SEQ ID NO: 1 or SEQ ID NO: 2 and can provide the construct with the ability to penetrate a cell membrane of eukaryotic cells (and more preferably with a nuclear transferability (nuclear membrane permeability)).

The amino acid sequence given by SEQ ID NO: 1 is a sequence provided by the addition of tryptophan-proline-cysteine (W-P-C) to the C-terminal side of the amino acid sequence given by SEQ ID NO: 4. Peptide comprising the amino acid sequence given by SEQ ID NO: 1 has a higher cell membrane permeability than peptide comprising the amino acid sequence given by SEQ ID NO: 4.

Peptide comprising the amino acid sequence given by SEQ ID NO: 4 is a variant of peptide comprising the amino acid sequence given by SEQ ID NO: 3, for which cell membrane permeability has been reported. Specifically, the 8th amino acid residue (asparagine residue) in the amino acid sequence with SEQ ID NO: 3 is replaced by a serine reside and the 9th amino acid residue (aspartic acid residue) is replaced by an asparagine residue. The present inventors have discovered that peptide comprising the amino acid sequence given by SEQ ID NO: 4 has a higher cell membrane permeability than peptide comprising the amino acid sequence given by SEQ ID NO: 3. The amino acid sequence given by SEQ ID NO: 3 is an NoLS that corresponds to the sequence segment (motif) composed of a total of 13 amino acid residues from the 491st amino acid residue to the 503rd amino acid residue of the LIM kinase 2 (LEVI kinase 2: Journal of Biological Chemistry, volume 281, number 35 (2006), pp. 25223-25230) present in human endothelial cells, which is a type of protein kinase that participates in intracellular signaling. The strength of cell permeability can thus be rated as SEQ ID NO: 3<SEQ ID NO: 4<SEQ ID NO: 1.

The amino acid sequence given by SEQ ID NO: 2 is a sequence provided by the addition of tryptophan-proline-cysteine (W-P-C) to the C-terminal side of the amino acid sequence given by SEQ ID NO: 5. Peptide comprising the amino acid sequence given by SEQ ID NO: 2 has a higher cell membrane permeability than peptide comprising the amino acid sequence given by SEQ ID NO: 5.

Peptide comprising the amino acid sequence given by SEQ ID NO: 5 is a variant of peptide comprising the amino acid sequence given by SEQ ID NO: 3. Specifically, the 8th amino acid residue (asparagine residue) and the 9th amino acid residue (aspartic acid residue) of the amino acid sequence given by SEQ ID NO: 3 are both replaced by the lysine residue. Peptide comprising the amino acid sequence given by SEQ ID NO: 5 was discovered by the present inventors to have a higher cell membrane permeability than peptide comprising the amino acid sequence given by SEQ ID NO: 3. The strength of the cell membrane permeability can thus be rated as SEQ ID NO: 3<SEQ ID NO: 5<SEQ ID NO: 2. In addition, peptide comprising the amino acid sequence given by SEQ ID NO: 5 has an excellent nucleolar transferability, and as a consequence the amino acid sequence given by SEQ ID NO: 2, which contains the amino acid sequence given by SEQ ID NO: 5, can be used as a nucleolar marker.

While the detailed mechanism is unclear, the cell membrane permeability can be enhanced by the addition of the WPC amino acid sequence to the C-terminal side of the cell membrane-permeable LIM kinase 2 NoLS (SEQ ID NO: 3) or its variants. Due to this, the amino acid sequence constituting the carrier peptide fragment of the herein disclosed foreign substance introduction construct can additionally be any of the following amino acid sequences:

KKRTLRKNDRKKRWPC, (SEQ ID NO: 6)

KKRTLRKKRRKKRWPC, (SEQ ID NO: 7)

KKRTLRKRKRKKRWPC, (SEQ ID NO: 8)

or

KKRTLRKRRRKKRWPC. (SEQ ID NO: 9)

The amino acid sequences given by SEQ ID NOs: 7 to 9 are amino acid sequences provided by the addition of the WPC amino acid sequence to the C-terminal side of the highly membrane-permeable LIM kinase 2 NoLS variants that have been discovered by the present inventors. The amino acid sequences given by SEQ ID NOs: 7 to 9 have excellent nucleolar transfer abilities and as a consequence can be used as nucleolar markers.

The herein disclosed "carrier peptide fragment" typically has the same amino acid sequence as the hereinabove-described amino acid sequences, but, insofar as the cell membrane permeability is not impaired, it encompasses sequences provided by modification of these amino acid sequences. These "modified sequences" are amino acid sequences (modified amino acid sequences) formed by the substitution, deletion, and/or addition (insertion) of one amino acid residue or a plurality of amino acid residues (typically two or three). Such slightly modified sequences can be readily used by an individual skilled in the art based on the herein disclosed information and as a consequence are encompassed by the "carrier peptide fragment" as a herein disclosed technical concept.

Representative examples of modified sequences in the present Specification are, for example, sequences produced by a so-called conservative amino acid replacement in which 1, 2, or 3 amino acid residues are conservatively replaced, as well as sequences in which 1, 2, or 3 amino acid residues have been added (inserted) to or deleted from a prescribed amino acid sequence. Typical examples of conservative substitutions are, for example, sequences in which a basic amino acid residue is substituted by a different basic amino acid residue (for example, exchange between a lysine residue and an arginine residue), and sequences in which a hydrophobic amino acid residue is substituted by a different hydrophobic amino acid residue (for example, exchange among the leucine residue, isoleucine residue, and valine residue).

The foreign substance introduction construct can be designed constructed by bonding (linking) a desired foreign substance, either directly or indirectly via a suitable linker, to the N-terminal side and/or the C-terminal side of the carrier fragment.

There are no particular limitations on the linker, and it may be a peptide linker or a nonpeptide linker. While not constituting a particular limitation, the amino acid sequence constituting a peptide linker preferably is an amino acid sequence that does not produce steric hindrance and is flexible. The peptide linker can be, for example, a linker that contains one or two or more amino acid residues selected from glycine, alanine, serine, and so forth and that is composed of not more than 10 amino acid residues (more preferably at least one to not more than five, for example, one, two, three, four, or five amino acid residues). β-alanine may be used for this linker. While not constituting a particular limitation, for example, an alkyl linker, polyethylene glycol (PEG) linker, aminohexanoyl spacer, and so forth may be used for the nonpeptide linker.

The foreign substance is typically an organic compound such as a polypeptide, nucleic acid, dye, or drug.

The foreign substance can be, for example, a polypeptide. When the foreign substance is a polypeptide, the target foreign substance introduction construct can be fabricated by designing a peptide chain that contains the amino acid sequence constituting this polypeptide and the amino acid sequence constituting the carrier peptide fragment, and by carrying out the biosynthesis or chemical synthesis of this peptide chain. In addition, foreign substance introduction constructs can be fabricated by the direct or indirect bonding to the N-terminal side and/or C-terminal side of the carrier peptide fragment, using various heretofore known chemical methods, of a nucleic acid, e.g., various DNAs and RNAs, a dye (for example, various fluorescent dye compounds, e.g., FAM, FITC), or an organic compound that functions as a drug (for example, antitumor agents, including nucleic acid-type antitumor agents, e.g., 5-fluorouracil (5FU), antivirals such as azidothymidine (AZT), and so forth).

While not being a particular limitation, the function possessed by the foreign substance can be, for example, promotion of an induction of stem cell differentiation (stem cell differentiation induction activity), inhibition of a proliferation of tumor cells (antitumor activity), inhibition of the proliferation of virus-infected cells (antiviral activity), and so forth.

There are no particular limitations on the number of foreign substances bonded to the carrier peptide fragment in the foreign substance introduction construct. Thus, one or more foreign substances may be bonded to one carrier peptide fragment. While not being a particular limitation, for example, a polypeptide, nucleic acid, drug, etc., may be bonded to the C-terminal side of one carrier peptide fragment and a dye may be bonded to the N-terminal side thereof. The bonding of a dye to the carrier peptide fragment facilitates evaluation of the efficiency of introduction into the eukaryotic cell of the foreign substance introduction construct as well as evaluation of localization within the cell, and is thus preferred.

When the foreign substance is a polypeptide, there are no particular limitations on the polypeptide (amino acid sequence) that may be adopted. For example, a polypeptide that has a relatively large number of amino acid residues, such as a polypeptide or protein that has approximately 100 to 1,000 amino acid residues, can be adopted as the foreign substance.

The total number of amino acid resides constituting the synthetic peptide that is fabricated as the foreign substance introduction construct is typically at least several to several tens (for example, 10), and is suitably not more than 1,000, preferably not more than 600, still more preferably not more than 500, and particularly preferably not more than 300 (for example, 10 to 300). Polypeptides of this length are easy to synthesize (biosynthesis, chemical synthesis) and easy to use.

The foreign substance is preferably a mature form of, or a precursor for (including proforms and pre-proforms), a polypeptide involved in a function such as development, differentiation, growth, malignant transformation, homeostasis, regulation of metabolism, and so forth in various cells and tissues (organs). In addition, through the introduction into a cell of a polypeptide for which the function is not yet known, the herein disclosed foreign substance introduction method can also be used to elucidate the function within a cell (within biological tissue) of the polypeptide.

For example, when the eukaryotic cell that is the target of foreign substance introduction is a human or other mammalian stem cell, it will be advantageous to use the mature form of, or a precursor for, a polypeptide having any of various biological activities involved with the induction of stem cell differentiation. Here, "stem cell" encompasses somatic stem cells, embryonic stem cells, and induced pluripotent stem cells (iPS cells in the following). When the eukaryotic cell that is the target of foreign substance introduction is a cancer cell (tumor cell), it will be advantageous to use various polypeptides involved in the induction of apoptosis of cancer cells (tumor cells). Or, in this case it will be advantageous to use a polypeptide that can prevent cancer cells (tumor cells) from suppressing the function of an immune surveillance system. When the eukaryotic cell that is the target of introduction is a bacterially infected cell or a virally infected cell, it will be advantageous to use various polypeptides involved with the induction of apoptosis of the infected cells, and/or polypeptides that can inhibit growth of the bacteria or virus in the infected cells, and/or polypeptides that can inhibit a broadening of the bacterial or viral infection from the infected cells.

Just as for the carrier peptide fragment, the polypeptide serving as the foreign substance may include, insofar as its function is preserved, a modified amino acid sequence formed by the substitution, deletion, and/or addition (insertion) of one or several amino acid residues.

In the foreign substance introduction construct in which a foreign substance is bonded to the C-terminal side of the carrier peptide fragment, preferably the α-amino group of the lysine on the N-terminal side of the carrier peptide fragment is acetylated. While a detailed mechanism is unclear, for many of the proteins in a eukaryotic cell the α-amino group of the amino acid on the N-terminal side is modified by acetylation, and due to this the intracellular stability of the construct can be enhanced if it has such a structure.

The amino acid residue on the C-terminal side of the foreign substance introduction construct is preferably converted to an amide. The structural stability (for example, protease resistance) of the construct in the cytoplasm and nucleolus can be improved when a carboxyl group of the amino acid residues (typically the C-terminal amino acid residue of the peptide chain) is converted to the amide. In addition, construct hydrophilicity is enhanced by carboxyl group amidation, and as a consequence the solubility of the construct in aqueous solvents can be improved. These aqueous solvents can be exemplified by water, various buffers, physiological saline (for example, PBS), and cell culture media.

For example, in the case of a foreign substance introduction construct in which a foreign substance is bonded to the N-terminal side of the carrier peptide fragment, the carboxyl group of the cysteine on the C-terminal side of the carrier peptide fragment is preferably converted to the amide. In addition, when, for example, the foreign substance is a polypeptide and this polypeptide is bonded to the C-terminal side of the carrier peptide fragment, the carboxyl group of the C-terminal amino acid residue of the polypeptide is preferably converted to the amide.

A foreign substance introduction construct having a relatively short peptide chain (including the polypeptide constituting the foreign substance, the carrier peptide fragment, and the peptide linker) can be readily produced based on general chemical synthesis methods. For example, a heretofore known solid-phase synthesis method or liquid-phase synthesis method may be adopted. A solid-phase synthesis method using Boc (t-butyloxycarbonyl) or Fmoc (9-fluorenylmethoxycarbonyl) as an amino group protection group is preferred. Thus, the aforementioned peptide chain having the desired amino acid sequence and modified moieties (e.g., N-terminal acetylation, C-terminal amidation, and so forth) can be synthesized by solid-phase synthesis using a commercial peptide synthesizer. Only a portion of the peptide chain may be synthesized by this method, for example, only the carrier peptide fragment, or a peptide chain containing the carrier peptide fragment and a peptide linker moiety may be synthesized by this method.

Alternatively, production may be carried out by biosynthesis of the peptide moiety based on genetic engineering methods. Thus, a polynucleotide (typically DNA) having a nucleotide sequence (containing the ATG start codon) encoding the desired amino acid sequence is synthesized. A recombinant vector having a gene expression construct comprising the synthesized polynucleotide (DNA) and various control elements (including a promoter, ribosome binding site, terminator, enhancer, and various cis elements that control the expression level) for bringing about the expression of the amino acid sequence in a host cell is constructed in correspondence to the host cell.

Using ordinary methods, this recombinant vector is introduced into a prescribed host cell (for example, yeast, insect cells, plant cells), and the host cell, or tissue or a specimen containing these cells, is cultured under prescribed conditions. The target peptide can thereby be produced in the cells. The peptide moiety is isolated from the host cell (from a medium when it has been secreted), and the target peptide moiety can be obtained by carrying out refolding, purification, and so forth, as necessary.

With regard to the method for constructing the recombinant vector, the method for introducing the constructed recombinant vector into a host cell, and so forth, methods already being used in this field may be directly adopted, and their detailed description has been omitted since these methods as such are not a particular characteristic feature of the present art.

For example, a fusion protein expression system can be adopted in order to bring about the efficient production of large amounts in a host cell. Thus, a gene (DNA) encoding the amino acid sequence of the target polypeptide is chemically synthesized, and the synthetic gene is introduced into an appropriate site in a suitable fusion protein expression vector (for example, the pET series available from Novagen, or a GST (glutathione S-transferase) fusion protein expression vector, such as the pGEX series available from Amersham Bioscience). A host cell (typically *E. coli*) is transformed with this vector. The resulting transformant is cultured to produce the target fusion protein. This protein is then extracted and purified. The obtained purified fusion protein is cleaved with a prescribed enzyme (protease), and the liberated target peptide fragment (i.e., the designed artificial polypeptide) is recovered by a method such as affinity chromatography. A desired foreign substance introduction construct (artificial polypeptide) can be produced using such a heretofore known fusion protein expression system (For example, the GST/His system provided by Amersham Bioscience can be adopted.).

Alternatively, a target polypeptide can be synthesized in vitro using a so-called cell-free protein synthesis system, by constructing a template DNA (i.e., a synthetic gene fragment that contains a nucleotide sequence encoding the amino acid sequence of the peptide moiety of the foreign substance introduction construct) for use in the cell-free protein synthesis system and by using the various compounds (ATP, RNA polymerase, amino acids, and so forth) required for synthesis of the peptide moiety. For example, the reports by Shimizu et al. (Shimizu et al., Nature Biotechnology, 19, 751-755 (2001)) and Madin et al. (Madin et al., Proc. Natl. Acad. Sci. USA, 97(2), 559-564 (2000)) are references for cell-free protein synthesis systems. At the time of the filing of the instant patent application, numerous enterprises were already performing contract polypeptide production based on the technology described in these reports and cell-free protein synthesis kits based on the technology described in these reports were commercially available (for example, kits can be acquired from CellFree Sciences Co., Ltd. in Japan).

A single-stranded or double-stranded polynucleotide containing the nucleotide sequence encoding the peptide moiety of the foreign substance introduction construct, and/or containing the nucleotide sequence complementary to this sequence, can be readily produced (synthesized) using heretofore known methods. Thus, the nucleotide sequence corresponding to this amino acid sequence can be readily determined and provided by selecting codons corresponding to the individual amino acid residues comprising the designed amino acid sequence. Once the nucleotide sequence has been determined, the polynucleotide (single-stranded) corresponding to the desired nucleotide sequence can be readily obtained using, for example, a DNA synthesizer. Using the obtained single-stranded DNA as a template, the target double-stranded DNA can be obtained using various enzymatic synthesis means (typically PCR). The polynucleotide may be in the form of DNA or in the form of RNA (e.g., mRNA). The DNA can be provided as the double strand or single strand. When provided as the single strand, it may be a coding strand (sense strand) or may be a noncoding strand (antisense strand) having the complementary sequence thereto.

The thusly obtained polynucleotide can be used as material for constructing a recombinant gene (expression cassette) for peptide production in various host cells or using a cell-free protein synthesis system, as described in the preceding.

The foreign substance introduction construct can be favorably used as an effective component in compositions that are applied based on the function of the foreign substance. The foreign substance introduction construct may take the form of a salt insofar as the function of the foreign substance is not impaired. For example, use can be made of an acid-addition salt that can be obtained using a common method by an addition reaction of a commonly used inorganic acid or organic acid. The "foreign substance introduction construct" described in the present Specification and in the claims thus encompasses these salt forms.

The foreign substance introduction construct can be provided in the form of a composition that can contain, in addition to the foreign substance introduction construct functioning as an effective component, any of various medically (pharmaceutically) acceptable carriers in accordance with the form of use.

A carrier as generally used in peptide drugs as, for example, a diluent, excipient, and so forth, is preferred for this carrier. This carrier can differ as appropriate in correspondence to the application and form of the foreign substance introduction construct, but is typically water, a physiological buffer solution, or any of various organic solvents. In addition, this carrier can be an aqueous solution of an alcohol (e.g., ethanol) at a suitable concentration, or can be glycerol or a nondrying oil such as olive oil, or may be a liposome. In addition, secondary components that can be incorporated in the drug composition can be exemplified by various fillers, expanders, binders, moisturizers, surfactants, dyes, fragrances, and so forth.

There are no particular limitations on the form of the composition. Typical forms can be exemplified by liquids, suspensions, emulsions, aerosols, foams, granules, powders, tablets, capsules, and ointments. In addition, for use as, inter alia, an injectable, a lyophilized material or granulated material can also be made in order to support the preparation of a drug solution by dissolution in, for example, physiological saline or a suitable buffer solution (for example, PBS) immediately prior to use.

The processes as such for the preparation of various drug formulations (compositions) using the foreign substance introduction construct (main component) and various carriers (secondary components) as materials may be based on heretofore known methods, and a detailed description of these formulation methods as such is omitted because they are also not a characteristic feature of the present art. For example, Comprehensive Medicinal Chemistry, edited by Corwin Hansch, Pergamon Press (1990) is a source of detailed information with regard to formulations.

The present disclosure provides a method, using the herein disclosed foreign substance introduction construct (composition), for introducing the foreign substance introduction construct within an organism (in vivo) or outside an organism (in vitro). In general terms, this method comprises the following steps (1) to (3):

(1) a step of preparing a foreign substance introduction construct having a carrier peptide fragment comprising either of the amino acid sequences given by SEQ ID NOs: 1 and 2 and having the foreign substance of interest bonded to the N-terminal side and/or the C-terminal side of the carrier peptide fragment;

(2) a step of supplying this foreign substance introduction construct to a sample that contains target eukaryotic cells; and (3) a step of incubating the sample to which the foreign substance introduction construct has been supplied, in order to introduce the construct into the eukaryotic cells in the sample.

With regard to in vivo, the "eukaryotic cells" here encompass, for example, various tissues, viscera, organs, blood, and lymph. With regard to in vitro, the "eukaryotic cells" here encompass, for example, various cell aggregates, tissues, viscera, organs, blood, and lymph removed from an organism, as well as cell lines.

For in vivo, compositions containing the hereinabove disclosed construct can be used in accordance with the methods and use amounts that correspond to the form of the composition and goals therefor. For example, precisely the desired amount can be administered as a liquid to a diseased region (for example, malignant tumor tissue, virally infected tissue, inflamed tissue) of a patient (i.e., an organism) by intravenous, intramuscular, subcutaneous, intradermal, or intraperitoneal injection. Alternatively, a solid form, e.g., a tablet, or a gel or aqueous jelly, e.g., an ointment, can be administered directly to a prescribed tissue (i.e., for example, a diseased region, e.g., a tissue or organ that contains, e.g., tumor cells, virally infected cells, or inflamed cells). Alternatively, a solid form, e.g., a tablet, can be administered orally. In the case of oral administration, the use is preferred of an encapsulating or protective (coating) material in order to prevent degradation by digestive enzymes in the digestive tract.

Alternatively, for eukaryotic cells that are cultured outside an organism (in vitro), a suitable amount of the herein disclosed composition (i.e., a suitable amount of the foreign substance introduction construct) may be supplied at least once to the culture medium for the target eukaryotic cells. The amount per supply and number of times of supply are not particularly limited because they can vary depending on conditions such as, for example, the type of eukaryotic cell being cultured, cell density (cell density at the start of culture), number of subcultures, culture conditions, and type of culture medium. For example, a single addition or a plurality of additions, i.e., twice or more, is preferably made so as to provide a carrier peptide fragment concentration in the culture medium within the range of approximately at least 0.05 μM to not more than 100 μM, for example, within the range of at least 0.5 μM to not more than 50 μM, and, for example, within the range of at least 1 μM to not more than 20 μM. The incubation time after construct addition is also not particularly limited since it can vary depending on the type of eukaryotic cell and various conditions. It can be, for example, at least 0.5 hour, at least 1 hour, at least 4 hours, at least 8 hours, or at least 20 hours. The incubation conditions are also not particularly limited because they can change depending on the type of eukaryotic cell, but, for example, incubation can be carried out at 37° C. in a 5% $CO_2$ atmosphere.

An example of an in vitro method of introduction is given in the examples below.

There are no particular limitations on methods for evaluating the efficiency of introduction of the foreign substance introduction construct. For example, when a dye (typically a fluorescent dye compound) is bonded to this construct, the efficiency of introduction into eukaryotic cells can be evaluated using microscopic observations (for example, fluorescence microscopic observations) or flow cytometry. The efficiency of construct introduction can also be evaluated by an immunochemical method (e.g., western blot or immune cell staining) that uses an antibody that specifically recognizes the peptide moiety of the construct.

Several examples relating to the present art are described in the following, but this should not be construed as limiting the present art to what is shown in these examples.

Fabrication of Foreign Substance Introduction Constructs

Synthetic peptides (peptides 1 to 4) having the amino acid sequences shown in Table 1 were prepared. Peptides 1 to 4 were all synthesized by carrying out solid-phase synthesis (Fmoc method) using a commercial peptide synthesizer and following the manual provided therewith. Peptides 1 to 4 were each synthesized with the α-amino group of the lysine on the N-terminal side being acetylated. A peptide (peptide 3') was synthesized by amidation of the carboxyl group on the arginine residue on the C-terminal side of peptide 3.

The procedure as such for using the peptide synthesizer is not a characteristic feature of the herein disclosed art, and a detailed explanation thereof has therefore been omitted.

TABLE 1

| Peptide No. | Sequence | SEQ ID NO: |
|---|---|---|
| 1 | KKRTLRKSNRKKRWPC | 1 |
| 2 | KKRTLRKKKRKKRWPC | 2 |
| 3 | KKRTLRKSNRKKR | 4 |
| 4 | KKRTLRKKKRKKR | 5 |

The fluorescent dye FAM ($C_{21}H_{12}O_7$:5(6)-carboxyfluorescein, molecular weight=376.3, excitation wavelength=495 nm, fluorescence wavelength=520 nm) was then directly bonded, based on a standard method, as the foreign substance to the amino acid residue on the C-terminal side of each of the peptides 1 to 4 (excluding peptide 3'). The following were obtained as a result: a foreign substance introduction construct provided with peptide 1 (also referred to as "sample 1"), a foreign substance introduction construct provided with peptide 2 (also referred to as "sample 2"), a foreign substance introduction construct provided with peptide 3 (also referred to as "sample 3"), and a foreign substance introduction construct provided with peptide 4 (also referred to as "sample 4"). A foreign substance introduction construct (also referred to as "sample 3'") was also obtained that was provided with peptide 3' and that had FAM directly bonded by a standard method to the N-terminal side of peptide 3'. Samples 1 to 4 were each diluted with DMSO to respectively prepare sample solutions 1 to 4 having a sample concentration of 2 mM.

Evaluation of the Cell Membrane Permeability by Flow Cytometry

The cell membrane permeability of peptides 1 to 4 was analyzed using HeLa cells (an established cell line derived from human cervical cancer cells) as the eukaryotic cells. As shown in Table 2, in this test the samples 1 to 4 prepared as described above were respectively used in Examples 1 to 4, while a FAM solution was used in Example 5.

TABLE 2

| | Constitution of the construct (addition) |
|---|---|
| Example 1 | Ac-KKRTLRKSNRKKRWPC-FAM |
| Example 2 | Ac-KKRTLRKKKRKKRWPC-FAM |
| Example 3 | Ac-KKRTLRKSNRKKR-FAM |
| Example 3' | FAM-KKRTLRKSNRKKR-CONH$_2$ |
| Example 4 | Ac-KKRTLRKKKRKKR-FAM |
| Example 5 | FAM |

Example 1

HeLa cells were cultured on DMEM (Dulbecco's modified Eagle's medium (Cat. No. 043-30085, from FUJIFILM Wako Pure Chemical Corporation)) containing 10% FBS (fetal bovine serum), which is a general culture medium.

The HeLa cells attached to the culture plate were washed with PBS, a 0.25% trypsin/EDTA solution was then added, and incubation was carried out for 3 minutes at 37° C. After this incubation, the aforementioned DMEM containing 10% FBS was added and the trypsin was inactivated, and the cells were then sedimented by carrying out centrifugal separation for 5 minutes at 150×g. The supernatant produced by the centrifugal separation was removed, and the aforementioned DMEM containing 10% FBS was added to the sediment (cell pellet) to prepare a cell suspension containing approximately $2 \times 10^5$ cells/mL. The cells were seeded (approximately $2 \times 10^5$ cells/well) by the addition of 1 mL of this cell suspension to the wells of a commercial 6-well plate (Iwaki). In addition, the 2 mM sample solution 1 was diluted with the aforementioned DMEM containing 10% FBS to prepare a sample solution 1 in which the sample 1 concentration was 20 µM. 1 mL of this 20 sample solution 1 was added to a well (i.e., the concentration of sample 1 in the culture medium in the wells was brought to 10 µM and the DMSO concentration was brought to 0.5%). The cells were subsequently incubated for 20 hours at 37° C. under the condition of 5% $CO_2$.

After this 20-hour incubation, the culture supernatant was removed from a well and the cells in the well were washed twice with 1 mL PBS. 200 µL of a 0.25% trypsin/EDTA solution was then added to the well and incubation was carried out for 3 minutes at 37° C. After this incubation, the trypsin was inactivated by the addition of 400 µL of the aforementioned DMEM containing 10% FBS to the well, and the cells were subsequently recovered by transferring the cell suspension in a well to a tube. The well was then washed by the further addition of 600 µL PBS to the well. The cells that had remained in the well were recovered to the tube by transferring the PBS in the well to the tube. Centrifugal separation was run on this tube for 5 minutes using conditions of 4° C. and 210×g. After the centrifugal separation, the supernatant was removed, the sediment (cell pellet) was suspended (washed) with 1 mL of PBS, and centrifugal separation was carried out using the same conditions as before. After this procedure had been performed twice, the supernatant was removed to obtain cells (cell pellet) that had been cultured on a sample 1-containing culture medium.

The cell permeability of sample 1 was analyzed using the resulting cells (cell pellet) and a flow cytometer. An On-Chip Flow Cytometer (On-chip Biotechnologies Co., Ltd.) was used for the flow cytometer.

For this analysis, the cell pellet obtained as described above was suspended in 50 µL PBS. To this suspension was added 50 µL of Sample Buffer 2× for use with the indicated flow cytometer to prepare a cell suspension for submission to analysis.

Gating was performed using this flow cytometer based on forward scatter (FSC) and side scatter (SSC); the gating was set for the cell population that was the target of the analysis; and the fluorescent intensity was measured for the cell population within this gating. The analysis was performed so the cell count for this cell population reached at least 10,000 or more. The FL2 fluorescence detector (optimal detection wavelength around 543 nm) on the indicated flow cytometer, which could detect the fluorescence wavelength of FAM, was used to measure the fluorescent intensity. The measurement results were analyzed using "FlowJo (registered trademark)" (Tree Star Inc.) commercial analysis software to obtain the mean fluorescent intensity (MFI) for the cell population that was the measurement target.

Example 2

This was carried out as in Example 1, except that the sample solution 2 was used in place of the sample solution 1.

Example 3

This was carried out as in Example 1, except that the sample solution 3 prepared as described above was used in place of the sample solution 1.

Example 3'

This was carried out as in Example 1, except that the sample solution 3' prepared as described above was used in place of the sample solution 1.

Example 4

This was carried out as in Example 1, except that the sample solution 4 prepared as described above was used in place of the sample solution 1.

Example 5

This was carried out as in Example 1, but using the DMSO-diluted FAM solution in place of the sample solution 1. A FAM solution concentration was used that provided the same concentrations as the sample 1 solution (i.e., the FAM concentration in the culture medium in the well=10 μM and the DMSO concentration=0.5%).

The results obtained in Examples 1 to 5 are given in Table 3 and FIG. 1. FIG. 1 is a graph that shows the value of the MFI in each example.

TABLE 3

|  | Example 1 | Example 2 | Example 3 | Example 3' | Example 4 | Example 5 |
|---|---|---|---|---|---|---|
| MFI | 87.5 | 121 | 12.4 | 62 | 24.3 | 10.3 |

As shown in FIG. 1, the MFI value was in each instance higher in Examples 1 to 4 than in Example 5. This shows that peptides 1 to 4 each have a cell membrane permeability and can introduce a foreign substance into a cell. The MPC in Example 1 was the highest among Example 1, Example 3, and Example 3'. This shows that the amino acid sequence (SEQ ID NO: 1) provided by the addition of the WPC amino acid sequence to the C-terminal side of the amino acid sequence given by SEQ ID NO: 4 has a better cell membrane permeability than peptide composed of the amino acid sequence given by SEQ ID NO: 4. Example 2 had a significantly higher MFI than Example 4. This shows that the amino acid sequence (SEQ ID NO: 2) provided by the addition of the WPC amino acid sequence to the C-terminal side of the amino acid sequence given by SEQ ID NO: 5 has a better cell membrane permeability than peptide composed of the amino acid sequence given by SEQ ID NO: 5.

While the detailed data are not provided, investigations by the present inventors have determined that not only in the case of the fluorescent dye, but also for the use of polypeptides, nucleic acids, and drugs as the foreign substance, such foreign substances are efficiently introduced from the cell exterior across the cell membrane and into the cytoplasm.

As is clear from the preceding, the herein disclosed foreign substance introduction construct is shown to have an excellent cell membrane permeability and as a consequence to be able to efficiently introduce a foreign substance of interest from outside a eukaryotic cell into at least the cytoplasm of the cell.

While specific examples of the herein disclosed art have been described in detail above, these are only illustrations and are not limitations on the claims. The art described in the claims encompasses various modifications and alterations of the specific examples provided above as illustrations.

The herein disclosed art provides an artificially fabricated construct for introducing a foreign substance of interest from the outside of a eukaryotic cell (particularly cell wall-free cells from various animals as represented by humans and other mammals) into the cytoplasm. Through the use of this construct, a foreign substance of interest can be effectively introduced into a target cell and cells can be obtained into which the foreign substance has been introduced, as can biological tissue, e.g., organs, that contains cells that contain the foreign substance. In addition, therapeutic agents against diseases can be provided through the use of this construct.

What is claimed is:

1. A method for introducing a foreign substance of interest from outside a eukaryotic cell into at least a cytoplasm of the cell, the method comprising:
    a step of preparing a foreign substance introduction construct that has
    a carrier peptide fragment comprising either of the following amino acid sequences:

KKRTLRKSNRKKRWPC (SEQ ID NO: 1)

KKRTLRKKKRKKRWPC (SEQ ID NO: 2)

and
    the foreign substance of interest bonded to an N-terminal side and/or C-terminal side of the carrier peptide fragment;
    a step of supplying the foreign substance introduction construct into a sample that contains a target eukaryotic cell; and
    a step of incubating the sample into which the foreign substance introduction construct has been supplied, to thereby introduce the construct into the eukaryotic cell in the sample.

2. The method according to claim 1, wherein the foreign substance is any organic compound selected from the group consisting of polypeptides, nucleic acids, dyes, and drugs.

3. The method according to claim 1, wherein the foreign substance is located on the C-terminal side of the carrier peptide fragment.

4. The method according to claim 3, wherein the α-amino group of the lysine residing at the N-terminal side of the carrier peptide fragment is acetylated.

5. The method according to claim 1, wherein the eukaryotic cell that is the target for the introduction of the foreign substance introduction construct is a human cell or a cell from a nonhuman mammal.

6. A foreign substance introduction construct for introducing a foreign substance of interest from outside a eukaryotic cell into at least the cytoplasm of the cell, comprising:
    a carrier peptide fragment comprising either of the following amino acid sequences:

KKRTLRKSNRKKRWPC (SEQ ID NO: 1)

KKRTLRKKKRKKRWPC (SEQ ID NO: 2)

and
    the foreign substance of interest bonded to the N-terminal side and/or the C-terminal side of the carrier peptide fragment.

7. The construct according to claim 6, wherein the foreign substance is any organic compound selected from the group consisting of polypeptides, nucleic acids, dyes, and drugs.

8. The construct according to claim 6, wherein the foreign substance is located at the C-terminal side of the carrier peptide fragment.

9. The construct according to claim 8, wherein the α-amino group of the lysine residing at the N-terminal side of the carrier peptide fragment is acetylated.

* * * * *